US00PP09230P

United States Patent [19]

Trees

[11] Patent Number: Plant 9,230

[45] Date of Patent: Aug. 1, 1995

[54] GERANIUM PLANT NAMED 'BFP-285 PINK PARFAIT'

[75] Inventor: Scott C. Trees, Arroyo Grande, Calif.

[73] Assignee: Geo. J. Ball, Inc., West Chicago, Ill.

[21] Appl. No.: 341,914

[22] Filed: Nov. 15, 1994

[51] Int. Cl.[6] ..... A01H 5/00
[52] U.S. Cl. ..... Plt./87.12
[58] Field of Search ..... Plt. 87.12

[56] References Cited

U.S. PATENT DOCUMENTS

P.P. 5,373 12/1984 Schumann ..... Plt./87.12

*Primary Examiner*—James R. Feyrer

*Attorney, Agent, or Firm*—Burns, Doane, Swecker & Mathis

[57] ABSTRACT

A new and distinct *Pelargonium*×*hortorum* cultivar named 'BFP-285 Pink Parfait is provided. This new Geranium cultivar was the result of a controlled breeding program wherein an unnamed plant designated 'A-S-M-1' was pollinated by an unnamed plant designated '4102A'. The new variety forms attractive semi-double florets having petals with a background color of lavender pink with a large dark purple freckle on each petal which fades to white at the attachment point. Medium green foliage is formed that commonly includes some zonation on younger leaves. The growth habit is medium self-branching and does not require the use of a growth regulator.

1 Drawing Sheet

SUMMARY OF THE INVENTION

The present invention comprises a new and distinct Geranium cultivar, botanically known as *Pelargonium*-×*hortorum* Bailey, and hereinafter is referred to by the cultivar name 'BFP-285 Pink Parfait.

The new cultivar is a product of a planned breeding program which had the objective of the creation of a new Geranium cultivar that exhibits uniform flowers, medium green foliage, a medium self-branching growth habit that requires no growth regulators, a propensity for rapid rooting, and a stable foliage coloration during shipment.

The breeding program that resulted in the production of the new cultivar of the present invention was carried out in a controlled environment during 1991 at Arroyo Grande, Calif., U.S.A. The female parent (i.e., seed parent) was a plant designated 'A-S-M-1' (non-patented in the United States) which exhibits single pink florets with a dark rose blotch on each petal and medium to light green foliage. The male parent (i.e., pollen parent) was a plant designated '4102A' (non-patented in the United States) which exhibits pink florets with medium green foliage. The parentage of the new 'BFP-285 Pink Parfait cultivar can be summarized as follows:

A-S-M-1×4102A.

'BFP-285 Pink Parfait' was discovered and selected during 1991 as a highly distinctive flowering plant from among the progeny of the stated cross at Arroyo Grande, Calif., U.S.A. This plant was intially designated BFP-285.

It was found that the new cultivar of the present invention:

(a) exhibts attractive semi-double florets having petals with a background color of lavender pink with a large dark purple freckle on each petal which fades to white at the attachment point,
(b) forms medium green foliage with some zonation on the younger leaves, and (c) exhibits a medium self-branching growth habit.

When a plant material of the 'BFP-285 Pink Parfait' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of 'BFP-285 Pink Parfait' was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1991 has demonstrated that the combination of characteristics as herein described for the 'BFP-285 Pink Parfait' cultivar is firmly fixed and is retained through successive generations of such asexual reproduction.

The new 'BFP-285 Pink Parfait' cultivar has not been observed under all possible environmental conditions. Accordingly, the described phenotype may vary significantly with variations in environments, such as temperature, light intensity, and day length.

Of the many commercial cultivars known to the originator of the new cultivar, the most similar is believed to be the 'Blues' cultivar. When the new cultivar of the present invention is compared to the 'Blues' cultivar, U.S. Plant Pat. No. 5,373, the 'BFP-285 Pink Parfait' cultivar is found to exhibit deeper lavender/pink florets (e.g., Red-Purple Group 69A vs. Red-Purple Group 68D), has fewer umbels per plant (e.g., 5 to 6 vs. 7 to 8), and smaller florets (e.g., 4.5 to 4.6 cm. vs. 4.9 to 5.0 cm.).

The new cultivar of the present inventions is being marketed by Geo. J. Ball, Inc. under the Designer trademark.

BRIEF DESCRIPTION OF THE PHOTOGRAPH

The accompanying photograph shows a typical plant of the new 'BFP-285 Pink Parfait' cultivar with colors being as nearly true as it is reasonably possible to make the same in a color illustration of this character. Typical flowers and foliage are depicted. The plant was grown in a greenhouse at West Chicago, Ill., U.S.A.

DETAILED DESCRIPTION

The following observations, measurements and comparisons describe plants grown in Ball FloraPlant's greenhouses located at West Chicago, Ill., U.S.A. under conditions which approximate those generally used in commercial practice. In the following description, color references are made to the R.H.S. Colour Chart of The Royal Horticultural Society, London, England. The color values were determined between 9:00 and 10:00 a.m. on Jul. 21, 1994, under natural light conditions of 2,000 footcandles.

Classification:

*Botanical.*—*Pelargonium*×*hortorum* Bailey, cv. 'BFP-285 Pink Parfait'.

*Commercial.*—Zonal Geranium.

INFLORESCENCE

A. Umbel:

*Average diameter.*—Approximately 10 to 11 cm. compared to approximately 9.7 to 11 cm. for the 'Blues' cultivar.

*Average depth.*—Approximately 5 to 6 cm. compared to approximately 5 to 7 cm. for the 'Blues' cultivar.

*Peduncle length.*—Approximately 13.5 to 14.5 cm. compared to 13.5 to 18.0 cm. for the 'Blues' cultivar.

*Pedicel length.*—Approximately 3.1 to 4.0 cm. compared to approximately 3.0 to 3.7 cm. for the 'Blues' cultivar.

*Number of umbels plant.*—When grown in a 10 cm. pot at 9 weeks after the sticking of a rooted cutting, there commonly are approximately 6 to 7 umbels per plant. This compares to approximately 10 to 11 umbels per plant for the 'Blues' cultivar. When plants are grown in the field for 16 weeks, the new cultivar commonly possesses approximately 13 umbels per plant while the Blues cultivar commonly possesses approximately 18 umbels per plant.

*Number of florets umbel.*—Plants grown in the greenhouse in 10 cm. pots commonly have approximately 25 to 30 florets per umbel at 9 weeks whereas plants of the 'Blues' cultivar grown in the same manner commonly have approximately 28 to 35 florets per umbel.

B. Corolla:

*Average diameter.*—Approximately 4.5 to 4.6 cm. compared to approximately 4.9 to 5.0 cm. for the 'Blues' cultivar.

*Form.*—Both the 'BFP-285 Pink Parfait' cultivar and the 'Blues' cultivar possess semi-double corolla with petaloids.

*Number of petaloids.*—Commonly possess 1 to 2 petaloids per floret whereas the 'Blues' cultivar only occasionally possesses 1 petaloid per floret.

*Color.*—General tonality from a distance of three meters: lavender pink with purple freckle and white eye. Adaxial: Red-Purple Group 68A with a patch of Red-Purple Group 66b and white attachment points. This compares to Red-Purple Group 68B with a patch of Red Group 52A for the 'Blues' cultivar. Abaxial: Red-Purple Group 69A. This compares to Red-Purple Group 68D for the 'Blues' cultivar.

C. Bud:

*Shape.*—Oval-rounded.

*Color.*—Adaxial: Red-Purple Group 68A. This compares to Red-Purple Group 68B for the 'Blues' cultivar. Abaxial: Red-Purple Group 69A. This compares to Red-Purple Group 68D for the 'Blues' cultivar.

D. Reproductive organs:

*Androecium.*—The anthers are commonly approximately 2 mm. in length. The pollen color is Orange-Red Group 30A for both the 'BFP-285 Pink Parfait' and the 'Blues' cultivars. The filaments are approximately 4 to 7 mm. in length.

*Gynoecium.*—The pistil length commonly is approximately 9 mm. There is a single stigma which commonly has a length of approximately 4 mm. which commonly branches into 5 parts, and the style length commonly is approximately 5 mm.

*Fertility.*—Usually does not produce fruits in the absence of mechanical fertilization.

E. Spring flowering response period: Approximately 6 to 7 weeks from rooted cuttings under greenhouse conditions.

F. Outdoor flower production: Freely flowering under outdoor growing conditions with substantially continuous blooming.

G. Durability: Ships well.

PLANT

A. Foliage: Dark green with faint zonation on young leaves.

*Form.*—Reniform, with a cordate base.

*Margin.*—Crenate.

*Color.*—Adaxial: Green Group 137A for both the 'BFP-285 Pink Parfait' and the 'Blues' cultivars. Young foliage of the 'Pink Parfait' cultivar exhibits a leaf base color of Green Group 137A with an area of Green Group 139A from the mid-point to the outer edges of leaves. Abaxial: Green Group 136A for both the 'BFP-285 Pink Parfait' and the 'Blues' cultivars.

*Size.*—Approximately 7.5 to 9.5 cm. at the widest point and approximately 6.1 to 7.5 cm. at the narrowest point. This compares to approximately 7.0 to 8.5 cm. at the widest point and 6.0 to 7.0 cm. at the narrowest point for the 'Blues' cultivar.

*Tolerance to Botrytis.*—None claimed.

B. General appearance and form:

*Internode length.*—Commonly varies from approximately 1.0 to 1.5 cm. compared to approximately 1.5 to 2.0 cm. for the 'Blues' cultivar.

*Branching pattern.*—Freely basal branching. No pinching is required to obtain self-branching. A medium self-branching growth habit is observed in the absence of the use of a growth regulator.

*Height.*—Commonly approximately 25 to 27 cm. above a 10 cm. pot at 9 weeks under greenhouse conditions compared to approximately 24 to 28 cm. for the 'Blues' cultivar.

What is claimed:

1. A new and distinct Geranium plant named 'BFP-285 Pink Parfait', substantially as herein shown and described, which:

(a) exhibits attractive semi-double florets having petals with a background color of lavender pink with a large dark purple freckle on each petal which fades to white at the attachment point, (b) forms medium green foliage with some zonation on younger leaves, and (c) exhibits a medium self-branching growth habit.

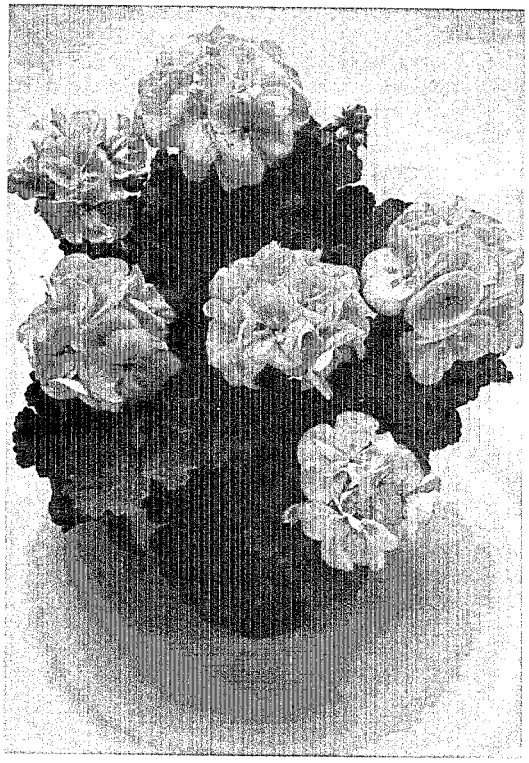

* * * * *